United States Patent [19]

Rasheed et al.

[11] Patent Number: 5,049,311

[45] Date of Patent: Sep. 17, 1991

[54] ALKOXYLATED ALKYL SUBSTITUTED PHENOL SULFONATES COMPOUNDS AND COMPOSITIONS, THE PREPARATION THEREOF AND THEIR USE IN VARIOUS APPLICATIONS

[75] Inventors: Khalid Rasheed, Missouri City; Rodney Cravey, Manvel; Paul D. Berger, Missouri City; Edwin O'Brien, Rosharon, all of Tex.

[73] Assignee: Witco Corporation, New York, N.Y.

[21] Appl. No.: 626,382

[22] Filed: Dec. 12, 1990

Related U.S. Application Data

[60] Continuation of Ser. No. 224,211, Jul. 22, 1988, abandoned, which is a division of Ser. No. 17,276, Feb. 20, 1987, abandoned.

[51] Int. Cl.[5] .............................................. C23F 11/10

[52] U.S. Cl. .......................... 252/389.52; 252/389.61; 252/389.62; 252/391; 252/395; 562/77

[58] Field of Search ............... 260/514 R; 252/389.53, 252/389.52, 389.61, 389.62, 391, 393, 390, 395; 262/77

[56] References Cited

U.S. PATENT DOCUMENTS

| | | | |
|---|---|---|---|
| Re. 30,796 | 11/1981 | Lesinski | 252/390 X |
| 2,166,136 | 7/1939 | Flett | 260/512 R |
| 2,828,334 | 3/1958 | Groote | 252/391 X |
| 3,004,006 | 10/1961 | King et al. | 260/79.3 |
| 3,716,488 | 2/1973 | Kolsky et al. | 252/155 |
| 3,809,717 | 5/1974 | Daeuble et al. | 260/512 R |
| 3,849,347 | 11/1974 | Tokiwa et al. | 252/545 |
| 4,018,278 | 4/1977 | Shupe | 166/252 |
| 4,029,702 | 7/1977 | Piccolini | 252/390 X |
| 4,071,746 | 1/1978 | Quinlan | 252/392 |
| 4,101,328 | 7/1978 | Fieser et al. | 252/390 X |
| 4,113,498 | 9/1978 | Rones et al. | 252/390 X |
| 4,197,091 | 4/1980 | Gainer | 252/390 X |
| 4,211,176 | 3/1982 | Sekmakas et al. | 524/555 |
| 4,313,837 | 2/1982 | Vukasovich et al. | 252/391 X |
| 4,324,674 | 4/1982 | Mackinnon | 252/78.5 |
| 4,328,149 | 5/1982 | Morse et al. | 524/458 |
| 4,344,871 | 8/1982 | Allaway et al. | 252/531 |
| 4,355,154 | 10/1982 | Saam et al. | 528/274 |
| 4,359,413 | 11/1982 | Ward et al. | 252/527 |
| 4,368,133 | 1/1983 | Forsberg | 252/75 |
| 4,370,256 | 1/1983 | Oakes | 252/391 |
| 4,372,882 | 2/1983 | Koster et al. | 252/529 |
| 4,375,416 | 3/1983 | Crisp et al. | 252/8.7 |
| 4,379,072 | 4/1983 | Yarham et al. | 252/389.62 X |
| 4,379,080 | 4/1983 | Murphy | 252/526 |
| 4,383,937 | 5/1983 | Williams | 252/389.62 X |
| 4,386,000 | 5/1983 | Turner et al. | 252/8.8 |
| 4,392,972 | 7/1983 | Mohr et al. | 252/392 X |
| 4,395,286 | 7/1983 | Sturwold | 252/391 X |
| 4,396,520 | 8/1983 | Payne et al. | 252/89.1 |
| 4,399,049 | 8/1983 | Gray et al. | 252/91 |
| 4,417,994 | 11/1983 | Stoddart | 252/135 |
| 4,430,243 | 2/1984 | Bragg | 252/91 |
| 4,437,898 | 3/1984 | Drosdziok et al. | 252/389.22 |
| 4,493,775 | 1/1985 | Coffey et al. | 252/8.555 |
| 4,501,589 | 2/1985 | Oschatz | 8/495 |
| 4,505,956 | 3/1985 | Yamamoto et al. | 427/393.1 |
| 4,514,320 | 4/1985 | Quinlan | 252/391 |
| 4,525,525 | 6/1985 | Höfer et al. | 524/742 |
| 4,539,140 | 9/1985 | Quinlan | 252/391 |
| 4,541,946 | 9/1985 | Jones et al. | 252/189 |
| 4,543,199 | 9/1985 | Kuntschik et al. | 252/75 |
| 4,574,061 | 3/1986 | Ries | 260/512 |
| 4,622,038 | 11/1986 | Login et al. | 8/115.6 |
| 4,628,836 | 12/1986 | Littman | 252/392 X |
| 4,675,125 | 6/1987 | Sturwold | 252/118 |
| 4,746,450 | 5/1988 | Frentrup et al. | 252/75 |
| 4,778,654 | 10/1988 | Bacskai et al. | 252/390 X |

OTHER PUBLICATIONS

Chemical Abstracts, vol. 104, 1986, p. 156, abstract No. 171224w, Greif et al., "*Surfactant Mixture and Its Use in Tertiary Oil Recovery*".

Chemical Abstracts, vol. 78, 1973, p. 80, abstract No. 17526j, Daeuble et al., "(*Hydroxyalkoxy*) *Benzenesulfonates as Leveling Agents in Dyeing of Polyamide Fibers with Acid Dyes*".

*Primary Examiner*—Deborah L. Kyle
*Assistant Examiner*—Valerie D. Fee
*Attorney, Agent, or Firm*—Lockwood, Alex, Fitzgibbon & Cummings

[57] ABSTRACT

The present invention relates to novel compounds of the formula $$M^{+}\ {}^{-}SO_3-C_6H_3(O(R_2)_nH)(R_1)$$

wherein $R_1$ is an alkyl group, $M^+$ is a cation, $R_2$ is an alkylene oxide and n is an integer from 1 to 4. Surfactant compositions containing these novel compounds, the process of preparing these novel compounds as well as the methods of using these surfactant compounds in enhanced oil recovery, as emulsifiers, in emulsion polymerization, as hydrotropes, in foamed drilling fluids, as dye carriers, as textile detergents, as foaming agents for concrete formation and as fiber lubricants are also disclosed.

6 Claims, No Drawings

ALKOXYLATED ALKYL SUBSTITUTED PHENOL SULFONATES COMPOUNDS AND COMPOSITIONS, THE PREPARATION THEREOF AND THEIR USE IN VARIOUS APPLICATIONS

This application is a continuation of application Ser. No. 224,211, filed July 22,1988, now abandoned, which is a division of application Ser. No. 017,276 filed Feb. 20, 1987, now abandoned.

BACKGROUND AND SUMMARY OF THE INVENTION

The present invention relates to new alkoxylated alkyl substituted phenol sulfonate compounds. Further, this invention relates to surfactant compositions containing these novel compounds, to a method for preparing these new alkoxylated alkyl substituted phenol sulfonate compounds and to a method for using these compositions in enhanced oil recovery, as emulsifiers, in emulsion polymerization, as hydrotypes, in foamed drilling fluids, as dye carriers, as textile detergents, as foaming agents for concrete formulations, and as fiber lubricants.

Petroleum is naturally recovered from subterranean formations in which it has accumulated by penetrating the formations with one or more wells and pumping or permitting the petroleum to flow to the surface through these wells. Recovery of petroleum from formations is possible only if certain conditions exist in the formations. The petroleum must be present in the formation in an adequately high concentration, and there must be sufficient permeability or interconnected flow channels within the formation to permit the flow of fluid if sufficient pressure is applied to the fluid. When the formation has natural energy present in the form of underlying active water drive, or gas dissolved in the petroleum which can exert pressure to drive the petroleum to the producing well, or a high pressure gas cap above the petroleum within the formation, this natural energy may be utilized to recover petroleum. Recovery of petroleum by utilization of natural energy is referred to as primary recovery. When this natural energy source is depleted, or in those instances where the formation does not contain sufficient natural energy to support primary recovery, some form of supplement or enhanced recovery process must be applied to the formation in order to extract petroleum therefrom.

Water flooding, which involves the injection of water into the subterranean, petroliferous formation for the purpose of displacing petroleum towards the producing well, is the most economical and widely practiced supplemental recovery method. Water does not displace petroleum with high efficiency, however, since water and oil are immiscible, and also because the interfacial tension between oil and water is quite high. This inherent weakness of water flooding has led to the introduction of many additives for decreasing the interfacial tension between the injection water and the formation petroleum. For example, polyglycol ether has been used as a surface active agent or surfactant to increase the capillary displacement efficiency of an aqueous flooding medium. Other surfactants which have been proposed for oil recovery operations include alkylpyridinium, alkylsulfates, alkylarylsulfates, ethoxylated alkyl or alkylaryl sulfates, alkylsulfonates, and alkylaryl sulfonates.

While the above described surfactants may be effective in surfactant recovery operations under ideal conditions, there are problems associated with the use of these materials in some petroleum containing formations. For example, the passage of an aqueous solution containing two totally different species of surfactants dissolved therein frequently results in the selective absorption of one material more than the other, or the absorption of one of the materials at a different rate than the other. Since the optimum performance of a multicomponent surfactant system is achieved only when the various surfactant species are all present in critical concentrations, this shift in concentration as a result of selective absorption of surfactant can result in there being non-optimum or even inoperative concentrations of surfactants at certain points in a formation.

Another problem which frequently degrades the performance received from surfactant flooding operations is associated with the formation temperature. Petroleum sulfonates as well as other alkyl or arylalkyl sulfonates are relatively stable at temperatures normally encountered in subterranean petroleum containing formations. However, these materials are usually not effective in the presence of high salinities and/or high formation water hardeners. Conversely, nonionic surfactants such as polyethoxylated alkyl phenols are effective for surfactant flooding in formations containing high salinity water or hard water, but these materials become insoluble at temperatures in the range of from about 100° to about 125° F., referred to as their cloud point. Thus, while the materials are not degraded permanently, they are removed from aqueous solution and therefore are ineffective so long as the temperature is above their cloud point.

It is widely recognized that hydrotropes are useful as additives by the detergent industry. Hydrotropes increase the solubility and the rate of dissolution of detergents in water. However, none of the hydrotrope additives currently in use by the detergent industry possesses the characteristics of increasing the solubility, the rate of dissolution as well as possessing good surfactant properties, such as low surface and interfacial tension.

Numerous attempts have been made, of course, to improve the solubility and rate of dissolution of a detergent in water by use of hydrotropes as additives. Further, a search for an hydrotrope additive that possesses the above described characteristics as well as possessing good surfactant properties has been made but such attempts have in general only met with limited success. Thus, the compounds of this invention, when added to a detergent, improve the solubility and rate of dissolution of the detergent in water. Additionally, these compounds possess good surfactant properties that allow the hydrotrope additive to increase the cleaning effect of the detergent as well as increasing the solubility and rate of dissolution of the detergent.

Various attempts have been made at inhibiting corrosion of metal surfaces and deposits thereof. This problem has a wide application in a variety of industrial settings. Various techniques have been employed in an attempt to prevent corrosion and inhibit deposition on metal surfaces. One method of preventing the corrosion and deposit has been a composition which combines a corrosion inhibiting amine and a surfactant that seems to provide increased corrosion inhibition to metal surfaces as well as possessing antifouling characteristics. While these compositions are a definite improvement over other prior art processes, the need still exists for a method of preventing corrosion of metal surfaces that still face many sectors of the manufacturing community.

The present invention overcomes the deficiency of prior art corrosion inhibitors by the addition of the novel alkoxylated alkyl substituted phenol sulfonate compounds. These compounds are soluble in kerosene and water making them excellent candidates for various industrial and manufacturing applications.

It is widely known to use various surfactants to emulsify monomers, such as styrene, vinyl chloride, vinyl acetate, acrylic and methacyrlic acid esters and others. Additionally, it is known to use surfactants to emulsify mixtures of monomers in water and in emulsions polymerized using free radical initiators such as sodium persulfate. However, the surfactants utilized in these various emulsion polymerization processes have not overcome all problems associated with these processes. For example, emulsion processes that employ organic solvents, instead of water as the solvent, still must face the additional problem of environmental pollution and meeting the increasingly stringent federal, state and local regulations with regard to pollution. Thus, a method of emulsion polymerization is needed that utilizes surfactants that have enhanced surfactant properties and can be used in a water based system in order to avoid the pollution problems of the prior art processes.

Various attempts at improving the characteristics of concrete formulation has long been sought by the industry. Due to the importance of concrete as a building material as well as its other uses, improved characteristics are essential in order to fulfill various new applications. Attainment of improved characteristics such as 1) improvement of workability and resulting reduction of water-cement ratio and the quantity of fine aggregate, 2) increase of the water-retaining force by air bubbles and resulting reduction of bleeding, and 3) improvement of pumpability are essential in the use and development of cement.

Several methods have been tried to attain these characteristics, the primary method includes the addition of highly oxidized resin acid salts, salts of protein substances, salts of alkyl benzenesulfonates and polyoxyethylene alkyl sulfates as well as various non-ionic surface active agents.

These methods, while successful in some respects, have not attained the improved properties still needed by the concrete industry. For example, the improvement of workability and reduction of water-cement ratio still persists.

Fiber finishing compositions are a necessary part of modern, high speed synthetic fiber manufacture. Virtually all operations performed on fibers following their being spun from the melt require the present of suitable fiber finishes to prevent snarling and breaking, thus enabling high fiber throughput. Generally speaking, a quality fiber finish must provide several often conflicting qualities. For example, the fiber finish must qualify for both the interaction between the fiber and the machinery on which it is processed and also the interactions among the fiber filaments themselves. This property is usually termed "lubricity" although in reality the change in the interactions caused by the fiber lubricant may sometimes result in a desirable increase in friction as well as the decrease in friction ordinarily associated with the term lubricant.

Prior art lubricants include material oils and waxes, fatty acid esters such as butyl stearate, vegetable oils and waxes, neoalcohol esters, silicones and polyoxyalkene polyethers. However, even relatively small amounts of residue that occur with these prior art lubricants can produce a resinous buildup on the heater plates at high process speeds. Thus, the requirement of a lower residue fiber lubricant suitable for high speed fiber processing is needed despite current fiber lubricants.

During the weaving of textiles, the warp threads are normally protected against breakage by application of a size. The presence of size on the warp threads interferes with finishing processes such as bleaching and dyeing and complete removal of size is highly desirable to obtain an even treatment such as even dyeing.

Various attempts at overcoming these problems have been made. For example, a process of applying a dyeing liquor or a printing paste that in addition to the dyestuffs includes non-ionic, amionic or cationic surfactants. These prior art processes, while improving the dyeing process, still has not overcome all problems associated with the dyeing process. Thus, the requirement of an improved dye carrier that lowers the amount of energy, time and additional chemicals are still needed.

As is well known, general purpose household detergents comprising a surfactant and a builder do not have sufficient power to remove oily dirt, and therefore, soiled materials washed therewith may yellow after storage for a long period of time. Heavily stained portions cannot be cleansed sufficiently by the usual washing process and, therefore, a more concentrated detergent solution is sometimes used. However, such a treatment is not preferred for general household use because of the difficulty of using same and/or it may damage the fabric or damage the shape of the clothing.

On the other hand, cleaning with solvents (dry cleaning) is suitable for removing oily dirt. However, this method has the disadvantage that water-soluble dirt and inorganic solid dirt cannot be removed. A system has been developed wherein a without detergent comprising a surfactant, a small quantity of water and a solvent is used. However, this system is not suitable for general household use, because a large quantity of a solvent is required.

U.S. Pat. No. 4,018,278 relates to an oil recovery process that utilizes a surfactant which is generally characterized as surfactant solution selected from water soluble salts of sulfonated ethoxylated alcohols and sulfonated ethoxylated alkylaryl compound and mixtures thereof. The surfactants of this reference are stable in formations whose waters contain concentrations of salt and/or divalent ions such as calcium and magnesium, as well as temperatures in excess of 120° F. The surfactants are preferably utilized as the sole constituent in an aqueous solution for use in oil recovery operations, or may be used in combination with an anionic surfactant such as petroleum sulfonate, alkyl sulfonate or alkylaryl sulfonate.

U.S. Pat. No. 2,828,334 discloses oxypropylated, oxyethylated, and oxybutylated derivatives of certain substituted phenol sulfonic acids and their salts as well as a method of making these compounds.

While the art has provided alkoxylated alkyl substituted phenol sulfonate compounds having a wide variety of properties, the need still exists for surfactant compounds having different and/or enhanced surfactant properties. For example, an important use of surfactants is in the enhanced hydrocarbon recovery operations. Further, many petroleum sulfonates are widely used as hydrotypes, dye carriers, foamed drilling fluids, textile detergents, fiber lubricants, in emulsion polymerization, and corrosion inhibitors. As is well known to those skilled in the art, petroleum sulfonates have recently emerged as the principal surfactants associated with enhanced oil recovery. However, these petroleum sulfonates when utilized in enhanced oil recovery operations must possess increased stability where the formation has temperatures in excess of 125° F. and has a high brine content.

Accordingly, it is one object of the present invention to provide novel alkoxylated alkyl substituted phenol sulfonate compounds.

Another object of this invention is to provide novel alkoxylated alkyl substituted phenol sulfonate compounds having enhanced surfactant properties.

A further object of this invention herein is to provide a new method in the preparation of these novel alkoxylated alkyl substituted phenol sulfonate compounds.

Still another object of this invention is to provide surfactant compositions containing these novel alkoxylated alkyl substituted phenol sulfonate compounds.

A still further object of this invention is to provide a method of using these novel surfactant composition in enhanced oil recovery operations.

Yet still another object of this invention is to provide a method of improving the solubility and rate of dissolution of detergents by the addition of these novel compounds.

A further object of this invention is to provide a method of improving corrosion inhibitors by the addition of these novel compounds.

A further object is to provide a method of improving emulsion polymerization by the addition of these novel compounds.

A still further object is to provide a method of improving concrete formation by the addition of these novel compounds.

Still another object of this invention is to provide a method of improving foamed drilling fluids by the addition of the novel compounds.

A still further object is to provide a method of improving dye carrier in textile by the addition of the novel compounds of this invention.

Yet another object of this invention is to provide a method of improving textile detergents by the addition of these compounds.

Still another object is to provide a method of improving fiber lubricants by the addition of these novel compounds.

These and other objects are achieved by alkoxylating alkyl substituted phenol sulfonates of the present invention. Briefly, this invention relates to novel alkoxylated alkyl phenol sulfonate compounds, novel surfactant compositions containing these novel compounds, the preparation of these surfactant compounds and compositions as well as the use of these surfactant compounds in enhanced oil recovery operations, as emulsifiers, in emulsion polymerization, as hydrotypes, in foamed drilling fluids, as dye carriers, as textile detergents, as foaming agents for concrete formation and as fiber lubricants. These compositions exhibit high thermal stability, low surface tension and low interfacial tension. These properties are contrary to the results expected from this type of alkoxylated alkyl substituted phenol sulfonate compositions.

In particular, this invention relates to compounds having the structural formula

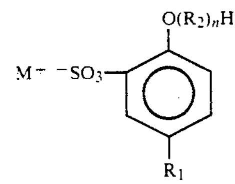

(1)

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4 with the provisio that when $R_2$ is ethylene oxide, then $R_1$ is an alkyl up having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

In another embodiment, this invention relates to surfactant compositions which include at least 90% of an aqueous medium and not more than 10% of a compound having the structural formula

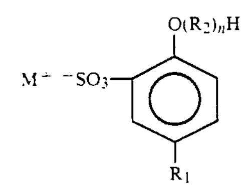

(1)

wherein $R_1$ is an alkyl group having about 8 to about 24 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is an alkyl group having at least n carbon atoms, and when $R_2$ is butylene oxide then $R_1$ is an alkyl group having at least 0.75 carbon atoms.

In still another embodiment, the compounds of this invention are prepared by a process comprising compounds having the structural formula

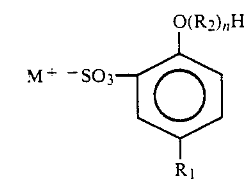

(1)

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is a whole number from about 1 to about 4, with the provisio that when $R_2$ is ethylene oxide, then $R_1$ is an alkyl group having at least 3 n carbon atoms, when $R_2$ is an alkyl group having at least n carbon atoms, and when $R_2$ is butylene oxide then $R_1$ is an alkyl group having at least 0.75 carbon atoms; which comprises the steps of (a) mixing a phenol having the formula

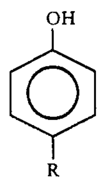

wherein $R_1$ has the same meaning as defined for formula (1), with a sulfonating agent to produce a sulfonic acid intermediate having the SO3H group in ortho position with respect to the OH group of said phenol material;

(b) adding a solvent to said acid intermediate;

(c) neutralizing said acid intermediate with a base to produce a sulfonate compound having the formula

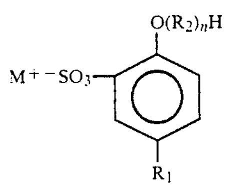

wherein $R_1$ and $M^-$ have the same meaning defined above following Formula (1); and (d) reacting said sulfonate with an alkylene oxide to produce the compound of Formula (1).

A still further embodiment of this invention relates to a method for hydrocarbon recovery from a subterranean formation comprising:

(a) injecting into at least one injection well a surfactant composition comprising at least 90% aqueous and not more than 10% of a compound having the structural formula

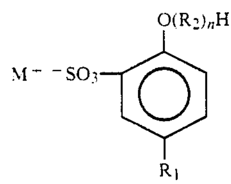

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is an alkyl group having at least n carbon atoms, and when $R_2$ is butylene oxide then $R_1$ is an alkyl group having at least 0.75 n carbon atoms.

(b) causing said injected surfactant composition to move from the injection well towards one or more production wells displacing hydrocarbon present in said formation; and (c) recovering displaced hydrocarbon from at least one of said production wells.

Yet in another embodiment, this invention relates to a method of improving the solubility and rate of dissolution of detergents which comprises adding to said detergents about 1% to about 10% weight of a compound having the general formula

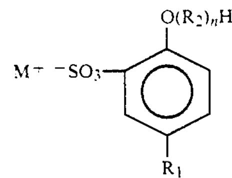

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Still another embodiment of this invention relates to a method of improving the effectiveness of corrosion inhibitors which comprises adding to said inhibitor about 1% to 10% of a compound having the general formula

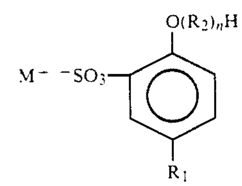

wherein $R_1$ is an alkyl group having about 8 to about 24 carbon atoms, $R_2$ is an alkylene oxide having about 2 to about 4 carbon atoms, $M^-$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

A further embodiment of this invention relates to improving the efficiency of emulsion polymerization which comprises adding to said polymerization about 1% to about 10% weight of a compound of the formula

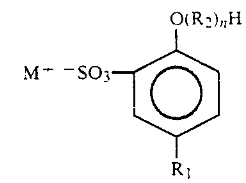

wherein $R_1$ is an alkyl group having about 8 to about 24 carbon atoms, $R_2$ is an alkylene oxide having about 2 to about 4 carbon atoms, $M^-$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Another embodiment of this invention relates to a method of improving concrete formation which comprises adding to about 1% to about 10% of a foaming agent of the formula,

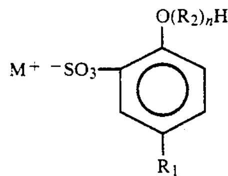

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Still a further embodiment of this invention relates to a method of improving drilling fluids which comprises adding to a foaming agent about 1% to about 10% by weight of a compound having the general formula,

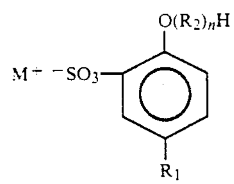

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Still in another embodiment, this invention relates to a method of preparing improved dye carriers in textiles which comprises adding to the carrier about 1% to about 10% weight of a compound of the formula

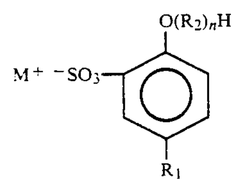

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Yet another embodiment of this invention relates to a method of improving textile detergents which comprises adding to said detergent about 1% to about 10% weight of a compound

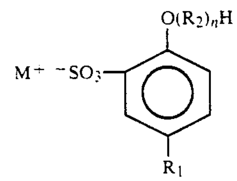

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

Yet a still further embodiment of this invention relates to a method of improving fiber lubricants which comprises adding to said lubricants about 1% to 10% weight of a compound having the general formula

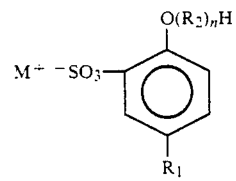

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4, with the provisio that when $R_2$ is ethylene oxide, then $R_1$ is an alkyl group having at least 3 n carbon atoms, when $R_2$ is propylene oxide, then $R_1$ is an alkyl group having at least n carbon atoms, and when $R_2$ is butylene oxide, then $R_1$ is an alkyl group having at least 0.75 n carbon atoms.

DETAILED DESCRIPTION OF THE INVENTION

Thus, in accordance with the present invention, there are provided alkoxylated alkyl phenol sulfonate compounds which can be identified from the following formula:

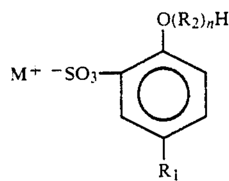

(1)

wherein $R_1$ is an alkyl group having about 8 to about 24 carbon atoms, $R_2$ is an alkylene oxide having about 2 to about 4 carbon atoms, $M^+$ is selected from the group consisting of Na, K, Li, Ca, Ba, Sr, Mg, Zn and amine salts thereof, and n is an integer from 1 to about 4. The positioning of the various substituents is essential in terms of the preparation and efficiency of the compounds. Thus, the aromatic hydrocarbon moiety has the $R_2$ group and the $R_1$ group in para position with respect to each other and the $SO^-{}_3M^+$ group in ortho position to the $R_2$ group.

Another essential feature of the compounds of this invention is the relationship between the number of moles of alkylene oxide present in the aromatic moiety of formula (1) and the number of carbon atoms in the alkyl group $R_1$ of formula (1). This relationship is essential because of the enhanced surfactant properties, such as high thermal stability, low interfacial tension, excellent lubricity and low surface tension, that can be attributed this feature. Specifically, when $R_2$ of formula (1) is ethylene oxide, then $R_1$ of formula (1) is an alkyl group having at least 3 n carbon atoms. Conversely, when $R_2$ of formula (1) is propylene oxide, then $R_1$ of formula (1) is an alkyl group having at least n carbon atoms and when $R_2$ of formula (1) is butylene oxide, then $R_1$ of formula (1) is an alkyl group having at least 0.75 n carbon atoms.

The compounds of this invention are generally mixed with an aqueous medium to form useful surfactant compositions. The aqueous medium contemplated within the scope of this invention include water, deionized water, brine as well as other types of aqueous mediums known to those skilled in the art. The aqueous medium consists of about at least 90% of the composition and the compounds not more than 10% of the composition. The compounds are usually present in an amount of about 1% to about 8% of the total surfactant composition. As is known to those skilled in the art, the precise percentage of compounds in the surfactant composition will vary with the conditions of a given application.

Sulfonation Reaction

In accordance with one embodiment of this invention, a process of preparing the sulfonated phenol material of this invention is provided. This process is characterized by a reaction between one or more alkyl substituted phenol compounds in a sulfonation reaction.

The starting material for the sulfonation reaction can be characterized by the formula

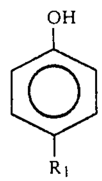

(1)

wherein $R_1$ and OH in para position to each other and —R is an alkyl group having 8 to 24 carbon atoms.

The sulfonation of the alkyl substituted phenol can be carried out in variety of ways which are generally known to those skilled in the art.

Among the sulfonation agents that can be used are fuming sulfuric acid, $SO_3$, a solution of $SO_3$ in $SO_2$, and concentrated sulfuric acid, with $SO_3$ being preferred. The sulfonation reaction is generally carried out utilizing a slight excess of the sulfonating agent. The reaction conditions include temperatures in the range of 100° F. to about 275° F., with about 120° F. to about 175° F. being preferred. The reaction time can be from a few minutes to several hours, with about several minutes to about 3 hours being preferred. The pressure for the sulfonation reaction is generally such that the ingredients remain in the liquid phase under the utilized temperature conditions.

The neutralization of the sulfonic acid intermediate formed in the sulfonation of the phenol starting material is advantageously carried out by mixing the sulfonated alkyl substituted phenol compound with a solvent. Solvents within the scope of this invention include xylene, aromatic 150, kerosene and diesel, with xylene, kerosene, and diesel being preferred. After the sulfonic acid and solvent are sufficiently mixed, the solution is neutralized by slowly adding a base. Further, it should be noted that the addition of a solvent, as described above, while being preferred, is not an essential feature in the preparation of the compounds of this invention. For example, the compounds may be prepared without the use of a solvent, while still retaining the enhanced properties set forth above. The bases contemplated within the scope of this invention that are particularly useful for the neutralization step include alkali metal oxides, alkali metal hydroxides, calcium carbonate, triethylamine, monoethylamine, diethylamine, tributylamine, n-propylamine, isoproylamine, n-butylamine and isobutylamine. The preferred bases are potassium oxides, potassium hydroxides, calcium carbonate, sodium oxides and sodium hydroxides. Any base employed in this neutralization step is usually in a slight stoichiometric excess. The bases should have a concentration in the range of about 25% and including the concentrated form of the base, with 35% to 60% bases being preferred. The neutralization step is generally carried out at a temperature in the range of 65° F. to about 275° F. However, as the base is added to the sulfonic acid intermediate xylene solution, the temperature will usually rise to about 175° F. to about 250° F. The pressure in this step is generally maintained to keep the reacting mass essentially in a liquid phase. The reaction is normally complete within a few minutes although longer time periods up to about 1 hour can be needed. Water can be removed from the product of the neutralization reaction by gradually increasing the temperature to a range of about 250° F. to about 320° F. This rise in temperature allows a sizable amount of water to be removed by azeotropic distillation or by any other distillation method.

Alkoxylation Reaction

The alkoxylation of the neutralized alkyl substituted phenol sulfonate material can be performed by reacting an alkylene oxide radical and a sulfonated alkyl substituted phenol.

The intermediate starting material for the alkoxylation reaction is a sulfonated phenol which can be broadly characterized as an alkyl substituted hydroxyaryl sulfonate. This intermediate material can also be characterized by the formula

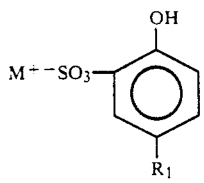

wherein $R_1$ is an alkyl group having 8 to 24 carbon atoms, $M^+$ being selected from the group consisting of Na, K, Li, Ca, Ba, Sr, Mg, Zn, and amine salt thereof, with the $SO^-{}_3M^+$ group in ortho position with respect to the OH group.

The alkoxylation of the alkyl substituted phenol sulfonate material can be carried out by any conventional method known to a person with ordinary skill in the art. However, in accordance with the present invention, an alkylene oxide such as ethylene oxide, propylene oxide and butylene oxide is added to alkyl substituted phenol sulfonate after it has been heated to about 210° F. to about 295° F., preferably about 240° F. to about 275° F. The alkylene oxide added to the alkyl substituted phenol is generally in stoichiometric excess. The alkoxylation reaction is generally carried out at a pressure of about 55 psi to about 85 psi, with about 65 psi to about 75 psi being preferred. The reaction time of this step is generally in the range of several minutes to about several hours, with about 30 minutes to about 3 hours being preferred.

Enhanced Oil Recovery Process

A still further embodiment of this invention resides in an enhanced oil recovery process. This process involves generally the conventional steps of enhanced oil recovery and the use of the novel surfactant composition as defined above. The enhanced oil recovery operation described below is intended to be merely for illustration purposes. The surfactant compositions of this invention are readily adaptable to most, if not all, enhanced oil recovery operations known to those skilled in the art.

In many enhanced oil recovery operations a preflush step preceding the use of any surfactant composition is generally carried out. Such preflush operations are generally known to those skilled in the art. Generally, an aqueous medium compatible with the surfactant system is injected via at least one injection well in the subterranean formation. The aqueous medium contemplated in this embodiment includes any aqueous medium known to those skilled in the art, but would include water and brine amongst others. The quantity of aqueous medium utilized in the preflush step usually depends on the various factors including previous hydrocarbon recovery operations, salinity of the formation, temperature of the formation, the depth of the formation as well as other factors generally known to those skilled in the art.

After the preflush step, if used, the surfactant compositions of this invention may be injected into the subterranean formation via at least one injection well. The surfactant composition is usually in the range of at least 90% of an aqueous medium and not more than about 10% of the surfactant compound, with about 1% to about 6% of surfactant being preferred.

The enhanced oil recovery operation makes use of the surfactant compositions which includes aqueous medium/alkoxylated alkyl substituted phenol sulfonate contemplated in this invention. These ingredients may be thoroughly mixed and then injected into the formation via one or more injection wells. However, the in situ formation of the ingredients in the formation, e.g. by simultaneous but unmixed injection or by alternating the injection of the surfactant and aqueous medium is also within the scope of this invention.

The present invention can be utilized for a variety of subterranean formations. The invention is, however, particularly well suited for formations containing a high brine content and temperatures in excess of 125° F.

Hydrotropes

Yet a further embodiment of this invention resides in a method of improving the solubility and rate of dissolution of detergents in water. It has been found that the alkoxylated alkyl phenol sulfonate compounds of this invention when added to a detergent increase the solubility and rate of dissolution of the detergent in water. Further, these compounds exhibit good surfactant properties such as low surface and interfacial tension. These compounds, when added to a detergent, provide an additive that increases the solubility, increases the rate of dissolution of a detergent in water, as well as possessing good surfactant properties. In essence, this additive fulfills the conventional use of hydrotropes by the detergent industry and additionally has surfactant properties that allow the additive to increase the cleaning characteristic property of the detergent.

The additives of this invention may be added to a given detergent in any way, appropriate to their physical form, as by mixing the components, co-agglomerating them or dispersing them in a liquid carrier. Preferably, the additives are in a dry, granular form and simply admixed with the detergent. However, it is within the scope of this invention to include spraying the additive, when in liquid form, onto any particulate component or components of the detergent which are capable of acting as carrier granules.

The additives of this invention are generally added to the detergent in a range of about 1% to about 10% weight to a corresponding amount of detergent. Preferably, the additives are added in a range of about 2% to about 5%. However, it should be noted that larger quantities of additives may be required under certain circumstances known to those skilled in the art.

The detergents within the scope of this invention include all of the conventional detergents known to those skilled in the art. The detergents may also contain all manner of additional material found in laundry and cleaning detergents. For examples, such additional material may include soil suspending agents such as carboxymethylcellulose and the like. Enzymes, especially the proteolytic, amylolytic and lysolytic enzymes commonly used in laundry detergent compositions, can also be present. Various perfumes, optical bleaches, fillers, anticaking agents, fabric softeners and the like can be present in the detergent to provide the usual benefits provided by the use of such materials. It is to be recognized that all such adjuvant materials are useful herein inasmuch as they are compatible and stable in the presence of the additives of this invention.

Corrosion Inhibitors

Another embodiment of this invention resides in a method of improving corrosion inhibition and deposition of particules on metal surfaces. It has been found that the alkoxylated alkyl phenol sulfonate compounds of this invention when added to an existing corrosion inhibitor increases the effectiveness of the inhibiting substance and further possess antifouling characteristics. The compounds of this invention exhibit enhanced surfactant properties, which allow the compounds when added to an inhibiting substance to improve the inhibiting effect and antifouling characteristic of the inhibitors. The use of the compounds of this invention, while enhancing the inhibiting and antifouling effects, generally requires that less of the inhibiting substance be utilized and still possess greater inhibiting and antifouling properties.

The compounds of this invention may be added to any corrosion inhibiting substance in a range of about 1% to about 10% weight, preferably about 2% to about 5% by weight. The inhibiting substances contemplated within the scope of this invention include primary, secondary and tertiary aliphatic or aromatic amines or derivative thereof. Additionally, the inhibiting substance can include any additional inhibiting substances known to those skilled in the art and that are chemically compatible with the compounds of this invention.

The inhibiting substance and compounds of this invention are generally prepared by, for example, mixing the corrosion inhibiting substances in an aqueous solution containing the compounds described above. Preferably, the inhibiting composition (inhibitor and compounds) is a stable solution capable of being stored for a long period of time without separation. The preferred aqueous solution is water, but may be other solutions depending on the inhibiting substance utilized and the specific application contemplated.

Application of the inhibit solution can be supplied by any conventional method depending on the circumstances. For example, the inhibiting solution can be supplied by conventional spray or atomizing nozzles or via other conventional techniques.

Fiber Lubricants

Still another embodiment of this invention relates to a method of improving fiber lubricants in fiber filaments in the production step and the processing step of synthetic fibers. It has been found that the alkoxylated alkyl phenol sulfonates of this invention when added as fiber lubricants in the process and production steps of synthetic fibers exhibit excellent lubricant property, antistatic property, and collecting property such as high speed unwinding from prin, resistance to attrition to metals and the like. These favorable properties are due to the enhanced surfactant properties exhibited by the compounds of the present invention.

The additive of this invention may be added to a fiber treating lubricant, but essentially the proportion may be in a range in which the effectiveness of the present invention can be exhibited; its content in the treating lubricant is usually in the range of about 1% to about 10% by weight, preferably in he range of about 2% to 5% weight.

The lubricating agent used together with the compounds of the present invention in the treating lubricant of the present invention can be selected from among purified mineral oils, synthetic fatty acid esters and polyoxyalkylene glycols. However, any conventional lubricant known to those skilled in the art are contemplated within the scope of this invention.

As purified mineral oils, those having a Redwood kinetic viscosity at 30° C. of 40 to 500 seconds may be used, and as the synthetic fatty acid esters, esters of aliphatic monobasic acids with aliphatic monohydric alcohols, esters of polyols such as ethylene glycol, diethylene glycol, neopentyl glycol, trimethylolpropane, glycerol, pentaerythritol, etc. with aliphatic monobasic acids or esters of aliphatic dibasic acids with aliphatic monohydric alcohols may be used.

Further concrete examples of the above-mentioned synthetic fatty acid esters are as follows:

Butyl stearate, n-octyl palmitate, 2-ethylhexyl palmitate, oleyl laurate, isohexadecyl laurate, isostearyl laurate, dioctyl sebacate, diisotridecyl adipate, ethylene glycol dioleate, trimethylolpropane trioctanoate, pentaerythritol tetraoctanoate. Further, as examples of polyoxyalkylene glycols, those obtained by subjecting propylene oxide and ethylene oxide to random or block addition polymerization to butanol, octanol, lauryl alcohol, stearyl alcohol or the like, those obtained by subjecting propylene oxide and ethylene oxide to random or block addition polymerization to propylene glycol, trimethylolpropane, glycerol, pentacrythritol, sorbitol or the like, etc., having various molecular weights, may be used.

Further, emulsification modifier, wetting agent, mildewproofing agent, and rustproofing agent, may be added to the above-mentioned various blend compositions, and the total amount of these additives is preferred to be 5% by weight or less based on the total blend composition.

The treating lubricant of the present invention, when applied to synthetic fibers as spinning lubricant or finishing lubricant, exhibits its effectiveness, and the lubricant, when used, is preferably attached to synthetic fibers in the form of an aqueous emulsion of 5 to 30% or in the form of a liquid obtained by diluting it with an organic solvent such as hydrocarbons, etc.

The treating lubricant of the present invention exhibits its effectiveness in the production and processing steps of thermoplastic synthetic fibers such as polyamides, polyesters, polypropylene, and it is particularly effective as spinning lubricant for polyester or polyamide filaments.

Emulsion polymerization

A further embodiment of this invention relates to a method for improving emulsion polymerization of various monomers. It has been found that the alkoxylated alkyl phenol sulfonate compounds of this invention when added to a conventional polymerization process are effective emulsifiers. Further, the compounds of this invention exhibit low foaming properties which are highly desirable and can be utilized with water as the solvent, as opposed to organic solvents, thus alleviating any enviromental pollution problems.

The compounds of this invention may be added to any compatible emulsion polymerization process in a range of about 1% to about 10% by weight, preferably about 2% to about 5% by weight.

The desired reactants and any polycondensation catalyst are emulsified by combining them with water. It is usually convenient to employ sufficient water to obtain a concentration of reactants of from about 5 to 80%, preferably from 10 to 50% based on the total weight of the reaction mixture.

Emulsification of the reactants can usually be achieved by stirring the mixture of reactants, polycondensation catalyst and water at room temperature. In some instances, particularly when employing relatively large quantities of reagents or ones which are not readily emulsifiable, it may be desirable to employ a mechanical homogenizer or ultrasonic device such as a sonic cell disruptor to prepare the emulsion.

Polymerization of the emulsified reactants is achieved by maintaining the emulsion at a temperature of from about 1° C. to the boiling point of the liquid phase for a period of time sufficient to achieve a substantially complete reaction or an equibrium distribution of molecular weight. Depending upon the reactants and the temperature of the reaction mixture, the time required will be from several minutes to 24 hours or more. The only precaution to be observed is that the reagent or reagents employed must be emulsifiable at the reaction temperature. So long as this criterion is met, any reaction temperature from above the freezing point, preferably above about 1° C. up to the boiling point of the aqueous phase can be employed. If the polymerization is conducted at superatmospheric pressure, the boiling point can be as high as 374° C. Normally, the temperature employed will be from 1° to 100° C., preferably from ambient to about 95° C.

Other criteria which determine the temperature range for a given polymerization reaction are the solubility of the reagents in water at the reaction temperature and the melting points of the reagents.

Foaming Agents In Concrete Formation

Still another embodiment of this invention resides in a method of improving the formation of concrete by the addition of a foaming agent. It has been found that the addition of the alkoxylated alkyl phenol sulfonate compounds of this invention increases the workability of the concrete, reduces the water-cement ratio, reduces the quantity of fine aggregate, increases the water retaining force by air bubbles and improves the pumpability of the concrete. The enhanced characteristics described above are attributable to the addition of compounds of this invention, which have low foam stability until combined with a hydrocarbon at which time, the compounds become excellent foaming agents.

The compounds of this invention may be added to concrete in a range of about 1% to about 10% by weight, preferably about 2% to about 5% by weight. The compounds of this invention may be incorporated by any number of methods. For example, the compounds may be mixed in water and then added to the concrete or in a dry form the compound may be mixed with the concrete emulsion of water.

The amounts of additives used in the present invention differ depending on the necessary quantity of air, the required slump, the kinds and amounts of cement and aggregate used, the mixing ratio of the respective materials, the kneading order, the kind and capacity of the kneading machine and the temperature, and they cannot be determined simply.

In the present invention, by controlling and adjusting the amount used of the foaming substance, the required air quantity of 3 to 6% specified according to the reinforced concrete construction standard (explanation), JASS 5 of Japanese Architectural Society or the required air quantity of 3 to 6% specified according to the standard indication of Japanese Civil Engineering Society can easily be obtained.

As the cement that can be used in the present invention, there can be mentioned, for example, Portland cements such as normal Portland cement, high-early-strength Portland cement, moderate heat Portland cement, white Portland cement and ultra-high-early-strength Portland cement, blended cements such as Portland blast-furnace cement, silica cement and fly ash cement, and special cements such as alumina cement and expansive cement. These cements may be used singly or in the form of a mixture of two or more of them, and in each case, good results can be obtained.

Dye Carriers

Still another embodiment of this invention resides in a method of an improved dye carrier in the weaving of textiles. It has been found that the alkoxylated alkyl phenol sulfonate compounds of this invention when added to existing dyestuffs improves the finishing processes and allows for an even treatment of the textile.

The compounds of this invention are generally added to the dyeing liquor or printing paste in an amount from about 1% to about 10% by weight, with about 2% to about 5% by weight being preferred.

Suitable textiles which can be dyed or printed according to the process of the invention include various fiber types and their blends, e.g. cellulosic textiles comprising natural or regenerated cellulose, for example, cotton, cellulose acetate, polyester, polyamides and polyacrylonitrile. The process of the invention is particularly advantageous for dyeing or printing textiles which are dyeable with disperse dyes, more preferably textiles comprising cellulose acetate especially cellulose triacetate or hemipentacetate.

The dyestuffs which may be used according to the process of the invention are selected in accordance with the affinity of the textile and the dyeing or printing conditions. Depending on the textile substrate anionic, cationic and disperse dyestuffs may be employed. However, as indicated above, disperse dyestuffs are preferred.

In addition to dyestuffs and components and the dyeing liquor or printing paste may contain further dyeing assistants, e.g. as conventionally employed for the dyeing or printing of the textiles listed above, for examples, a buffer, ammonium sulphate, acetic or formic acid, sodium dihydrogenphosphate, thickening agent, urea, reduction inhibitor, a carrier and the like. It may in particular be recommended to add one or more organic solvents to the dyeing liquor in order to dissolve the waxes, oils and fats from the substrate, including the oil staining from the weaving machine. Such organic solvents are known. Preferred organic solvents are glycols e.g., hexylene glycol, and white spirit. The amount of organic solvents added may be up to 50%, preferably from 10 to 20%, by weight based on the total weight of the added size and dyeing assistants.

The dyeing and printing can be carried out according to known methods. Dyeing may be effected by exhaust as well as continuously, for example, at a temperature from room temperature to H.T. conditions (about 140° C.) Fixation of the dyeings or printings may be carried out in accordance with known methods, e.g. at a temperature of from room temperature to 230° C. for 1 second to 48 hours, with saturated or superheated steam or hot air, under pressure or normal pressure conditions, optionally with an intermediary drying step. The sizes textiles may, for example, be dyed or printed according to the Pad-Roll, Pad or Print-Steam, Pad or Print-Thermofixation procedures, the methods of a minimum liquor application such as foam application or spraying, and the like.

After fixation of the dyeings and printings, the textiles are after-treated in a known manner, e.g. conventionally soaped or subjected to reductive after-clearing, rinsed and dried. Complete removal of the size takes place simultaneously during the conventional after-treatment subsequent to fixation.

According to a preferred embodiment of the invention the sized textile, preferably cellulose acetate, especially hemipentaacetate is dyed in accordance with the Pad-Roll method at a temperature from 60° to 90° C., preferably from 70° to 80° C., the storage period being from 5 minutes to 4 hours, preferably from 2 to 3 hours.

As a result of the process of the invention, the textile substrate is simultaneously de-sized and evenly dyed or printed.

Textile Detergents

Another embodiment of this invention resides in a method of improving textile detergents. It has been found that the alkoxylated alkyl phenol sulfonate compounds of this invention when added to an existing textile detergent increases the cleaning effects of the detergent as well as possessing enhanced surfactant properties. These properties, such as low surface and interfacial tension, increase the solubility and rate of dissolution of the detergent.

The compounds of this invention may be added to any conventional detergent in a range of about 1% to about 10% by weight, preferably about 2% to about 5% by weight.

The additives of this invention may be added to a given detergent in any way, appropriate to their physical form, as by mixing the components, co-aggolmerating them on dispersing them in a liquid carrier. Preferably, the additives are in a dry, granular form and simply admixed with the detergent. However, it is within the scope of this invention to include spraying the additive, when in liquid form, onto any particulate component or components of the detergent which are capable of acting as carrier granules.

The detergents within the scope of this invention include all of the conventional detergents known to those skilled in the art. The detergents may also contain all manner of additional material found in laundry and cleaning detergents. For examples, such additional material may include soil suspending agents such as carboxymethylcellulose and the like. Enzymes, especially the proteolytic, amyloytic and lysolytic enzymes commonly used in laundry detergent compositions, can also be present. Various perfumes, optical bleaches, fillers, anticaking agents, fabric softeners and the like can be present in the detergent to provide the usual benefits occasioned by the use of such materials. It is to be recognized that all such adjuvant materials are useful herein inasmuch as they are compatible and stable in the presence of the additives of this invention.

Foamed Drilling Fluids

Yet another embodiment of this invention relates to a method of improving foamed drilling fluids. It has been found that the alkoxylated alkyl phenol sulfonate compounds of this invention increase the effectiveness of the fluid and additionally exhibits the highly desirable characteristic of excellent foaming properties, when in the presence of hydrocarbons.

The compounds of this invention may be added to any conventional drilling fluid in a range of about 1% to about 10% by weight, preferably about 2% to about 5% by weight. The drilling fluids contemplated within the scope of this invention includes any chemically compatible drilling fluid known to those skilled in the art.

The drilling fluid may additionally contain other components, such as other corrosion inhibitors or the like as may be needed in a specific application. The compounds of this invention are readily adaptable to a wide variety of use characteristics depending on the circumstance surrounding the intended application.

The drilling fluid composition may be admixed in any aqueous medium or each component can be injected in a well separately or in various combinations. For example, the compounds of this invention may be admixed with any aqueous medium and injected in the well prior to or after the conventional drilling fluid is added.

It should be recognized that precise conditions and requirements in the use of this improved foamed drilling fluid depends largely upon conditions of its intended application.

Emulsifiers

A still further embodiment of this invention resides in a method of utilizing the compounds of this invention as emulsifiers. It has been found that the alkoxylated alkyl phenol sulfonate compounds form stable emulsion with considerable foaming when diesel, xylene or kerosene are utilized as solvents.

The emulsifiers of this invention are generally prepared by utilizing about 40% to about 60% of the desired solvent, about 40% to about 60% of an aqueous medium and about 1% to about 10% of the compounds of this invention. It should be understood that precise amounts of the various components may vary depending on the intended application.

Additional components may be utilized in the emulsifier of this invention. The additional components within the scope of this invention may include non-ionic emulsifiers of the type derived from polygols, particularly polyoxyethylene glycol or polyoxypropylene glycols as well as others.

Depending upon the intended application, various mixing procedures may be employed. For example, if a toxicant is utilized, it is preferable to dissolve the toxicant in the solvent and stir until the mixture is clear. The emulsifier is then added and stirred until clear. In use, teh desired or requisite amount of toxicant concentrate is poured into the predetermined amount of water and the resulting emulsion is ready for application to the surfaces to be treated by spraying or any other desired manner. It should be understood that the utility extends to all folds where emulsions oleaginous and aqueous materials are desired.

For a better understanding of the present invention, together with other and further objections, reference is made to the following descriptions and examples.

EXAMPLE 1

This example describes the preparation of the sodium salt of ethoxylated nonylphenol sulfonic acid.

Nonylphenol, wherein the nonyl group is in para position with respect to the OH group, was sulfonated in a continuous pilot unit (a glass reactor) at 154° F. with sulfur trioxide (4% by volume in 96% air). The resulting product was a dark viscous liquid with an acid number of 175-195 and a CID active of 78-81%. In a five liter glass round bottom flask equipped with a receiver to collect distillate and a mechanical stirrer, 1458 grams (4.79 moles) of nonylphenol sulfonic acid and 1841 grams of xylene were stirred. To this mixture 428 grams (5.35 moles) of 50% sodium hydroxide was slowly added with the temperature rising to about 198° F. This resulted in the product having a dark amber color with the base number of 4.4. The resulting solution was gradually heated to about 287° F. while azeotroping off 332 grams of water. In a two gallon Parr pressurized reactor, 3043 grams (4.82 moles) of the diluted sodium salt of nonylphenol sulfonic acid was heated to a 255° F. under a nitrogen blanket. At a range of between 255°–265° F., 1113 grams (25.2 moles) of ethylene oxide was added at 70 psi. The product was a slightly hazy liquid with a Gardner color of 18, a base number of 4.1, a hydroxyl number of 63.6 and a corrected solids hydroxyl number of 98.5. This indicated that 5.5 moles of ethylene oxide was added to each available hydroxyl. NMR spectra confirmed formation of the expected product, sodium salt of nonylphenol sulfonic acid.

Further ethoxylation of the product gave a base number of 3.2, a hydroxyl number of 53.6, solids corrected hydroxyl number of 77.6. This indicates that 9.0 moles of ethylene oxide was added to each available hydroxyl.

EXAMPLE 2

The example describes the preparation of calcium salt of ethoxylated nonylphenol sulfonic acid.

Nonylphenol, wherein the nonyl group was in para position with respect to the OH group, was sulfonated in a continuous pilot unit (a glass reactor) at 155° F. with sulfur trioxide (4% by in 96% air). The resulting product was a dark viscous liquid with an acid number of 175–195 and a acid active of 78–81%. In a two liter glass round bottom flask, 61.4 grams of charged $CaCO_3$ and 635 grams of xylene was heated to 140° F. In a separate flask, 373.6 grams of nonylphenol sulfonic acid and 75 grams of xylene were mixed and then added slowly to the healed $CaCO_3$ xylene solution. 12 grams of $H_2O$ were added to this mixture and heated to 175° F. An additional 35 grams of xylene was used to wash down the nonylphenol sulfonic acid. 3 grams of $CaCO_3$ and 32 grams of 45% KOH was to added to this product. The resulting product was heated to distill off $H_2O$ and filtered at room temperature with 541 grams of filtered product transferred to a one liter flask with a small quantity of xylene added. This product was heated to 285° F. to dehydrate. After heating, 446 grams of product was transferred to another two liter flask where 213 grams of ethylene oxide was added at a temperature in range of about 255° F. to about 275° F. The final product had a base number of 4.96, hydroxyl number of 78.1, and a corrected solids number of 131.7. This indicated that 2.3 moles of ethylene oxide was added to each available hydroxyl.

EXAMPLE 3

The following data illustrates the interfacial tension of the Water-Blandol System utilizing fresh and aged samples (1% in deionized water). The compounds in Table I was prepared in accordance with the procedure in Example 1, except dodecylphenol sulfonic acid was substituted where indicated below. In the absence of surfactant, the interfacial tension of Water-Blandol system is 52 dynes/cm.

TABLE I

| | Interfacial Tension (dynes/cm) | | |
|---|---|---|---|
| Sample | Initial | 7 days at 400° F. | 14 days at 400° F. |
| 1. NPSA + 4EO Na Salt | 3.96 | 2.16 | 2.11 |
| 2. NPSA + 6EO Na Salt | 4.37 | 2.84 | 2.94 |
| 3. NPSA + 2EO Na Salt | 3.12 | 1.62 | 1.53 |
| 4. DPSA + 8EO Na Salt | 5.88 | 4.59 | 4.75 |
| 5. DPSA + 2EO Na Salt | 2.79 | 2.07 | 2.18 |
| 6. DPSA + 6EO Na Salt | 5.44 | 4.46 | 4.54 |
| 7. DPSA + 4EO Na Salt | 4.34 | 3.45 | 3.91 |

Legend:
NPSA - Nonylphenol sulfonic acid
DPSA - dodecylphenol sulfonic acid
EO - ethylene oxide The results shown in Table I illustrate that the compounds 1 to 7 have relatively low interfacial tension at seven and fourteen days at 400° F. when compared to the initial reading without prejudice.

EXAMPLE 4

The following data illustrates the thermal stability and hydrolytic stability at 400° F. The compounds in Table II were prepared in accordance with the procedure in Example 1 except dodecylphenol sulfonic acid was substituted below where indicated.

TABLE II

| | Initial | | 1 day | |
|---|---|---|---|---|
| Sample | Activity | pH | Activity | pH |
| 1. NPSA + 4EO Na Salt | 1.638 | 9.7 | 1.596 | 9.1 |
| 2. NPSA + 6EO Na Salt | 1.344 | 9.8 | 1.313 | 9.2 |
| 3. NPSA + 2EO Na Salt | 1.995 | 9.9 | 1.932 | 9.2 |
| 4. DPSA + 8EO Na Salt | 1.218 | 9.7 | 1.187 | 8.9 |
| 5. DPSA + 2EO Na Salt | 1.869 | 10.1 | 1.848 | 9.6 |
| 6. DPSA + 6EO Na Salt | 1.344 | 9.8 | 1.313 | 8.4 |
| 7. DPSA + 4EO Na Salt | 1.575 | 7.9 | 1.533 | 6.8 |
| | 2 days | | 4 days | |
| Sample | Activity | pH | Activity | pH |
| 1. NPSA + 4EO Na Salt | 1.586 | 8.4 | 1.575 | 7.9 |
| 2. NPSA + 6EO Na Salt | 1.292 | 8.9 | 1.292 | 7.4 |
| 3. NPSA + 2EO Na Salt | 1.932 | 9.0 | 1.932 | 8.5 |
| 4. DPSA + 8EO Na Salt | 1.187 | 8.6 | 1.176 | 8.0 |
| 5. DPSA + 2EO Na Salt | 1.848 | 9.4 | 1.848 | 9.0 |
| 6. DPSA + 6EO Na Salt | 1.292 | 6.8 | 1.292 | 7.2 |
| 7. DPSA + 4EO Na Salt | 1.523 | 7.0 | 1.502 | 7.1 |
| | 7 days | | 14 days | |
| Sample | Activity | pH | Activity | pH |
| 1. NPSA + 4EO Na Salt | 1.565 | 7.4 | 1.526 | 7.3 |
| 2. NPSA + 6EO Na Salt | 1.260 | 6.4 | 1.166 | 6.3 |
| 3. NPSA + 2EO Na Salt | 1.932 | 8.3 | 1.861 | 7.6 |
| 4. DPSA + 8EO Na Salt | 1.145 | 7.1 | 1.128 | 6.9 |
| 5. DPSA + 2EO Na Salt | 1.827 | 8.1 | 1.774 | 7.6 |
| 6. DPSA + 6EO Na Salt | 1.292 | 8.1 | 1.290 | 7.2 |
| 7. DPSA + 4EO Na Salt | 1.470 | 6.2 | 1.451 | 5.0 |

*Activity expressed in milliequivalents/gram.
Legend:
NPSA - nonylphenol sulfonic acid
DPSA - dodecylphenol sulfonic acid
EO - ethylene oxide The results shown in Table II illustrate that the compounds 1 to 7 had excellent thermal and hydrolytic stability when viewed over the 14 day period at 400° F.

EXAMPLE 5

This example illustrates the surface tension of sample compounds aged at 400° F. The compounds of Table III were prepared in accordance with the procedure in Example 1, except dodecylphenol sulfonic acid was substituted where indicated below.

TABLE III

| Sample 400° F. | Initial | 2 days | 4 days | 7 days | 14 days |
|---|---|---|---|---|---|
| 1. NPSA + 4EO Na Salt | 30.47 | 30.47 | 33.56 | 30.62 | 30.39 |
| 2. NPSA + 6EO Na Salt | 31.98 | 30.85 | 31.60 | 31.53 | 30.92 |
| 3. NPSA + 2EO Na Salt | 30.32 | 29.9 | 29.41 | 29.11 | 28.89 |
| 4. DPSA + 8EO Na Salt | 34.17 | 33.26 | 33.18 | 32.96 | 33.34 |
| 5. DPSA + 2EO Na Salt | 29.56 | 30.39 | 28.89 | 29.72 | 28.96 |
| 6. DPSA + 6EO Na Salt | 32.96 | 32.38 | 33.18 | 32.43 | 31.75 |
| 7. DPSA + 4EO Na Salt | 31.98 | 30.39 | 30.83 | 31.45 | 30.92 |

Legend:
NPSA - nonylphenol sulfonic acid
DPSA - dodecylphenol sulfonic acid
EO - ethylene oxide
Surface tension determined at 1% concentration The data shown in Table III illustrates the low surface tension results even after 2 weeks at temperatures of 400° F.

EXAMPLE 6

This example illustrates the lubricity of compounds in Table IV utilizing a Baroid lubricity tester. The compounds in Table IV were prepared in accordance with the procedure of Example 1, except dodecylphenol sulfonic acid was substituted where indicated below.

TABLE IV

| Sample | Water | In/lb.Torque 0.5% Surfactant | Percent Torque Reduction |
|---|---|---|---|
| 1. NPSA + 4EO Na Salt | 38 | 16 | 58 |
| 2. NPSA + 6EO Na Salt | 38 | 12 | 68 |
| 3. NPSA + 2EO Na Salt | 38 | 14 | 63 |
| 4. DPSA + 8EO Na Salt | 36 | 16 | 56 |
| 5. DPSA + 2EO Na Salt | 36 | 15 | 58 |
| 6. DPSA + 6EO Na Salt | 38 | 15 | 60 |
| 7. DPSA + 4EO Na Salt | 38 | 15 | 60 |
| 8. Witconol NP-100 Nonylphenol with 10 mole EO | 36 | 35 | 3 |
| 9. Witcolate D51-53 Sodium Sulfate Salt | 38 | 14 | 63 |

Legend:
NPSA — nonylphenol sulfonic acid
DPSA — dodecylphenol sulfonic acid
EO — ethylene oxide
Percent torque reduction was calculated by the following formula:

$$\% \text{ Torque Reduction} = \frac{W - A}{W}$$

W = In/lb. Torque deionized water
A = In/lb. Torque 0.5% surfactant in deionized water.

The data shown above illustrates the excellent lubricity characteristics of all compounds 1 to 7. Witconol Np-100 was included as a core surfactant and Witcolate D51-53 as the sodium sulfate salt of NP-100, which represented a similar type chemical structure.

EXAMPLE 7

This example illustrates the foam stability of compounds of 1 to 7 when 0.5 ml of 50 exp. dissolved in 100 ml tap-water. The compounds in Table V were prepared in accordance with the procedure of Example 1, except dodecylphenol sulfonic acid was substituted where indicated below.

TABLE V

| Sample | Foam Height (ml) | Half-Life (sec.) |
|---|---|---|
| 1. NPSA + 4EO Na Salt | 200 | 88 |
| 2. NPSA + 6EO Na Salt | 230 | 81 |
| 3. NPSA + 2EO Na Salt | 230 | 84 |
| 4. DPSA + 8EO Na Salt | 290 | 95 |
| 5. DPSA + 2EO Na Salt | 400 | 113 |
| 6. DPSA + 6EO Na Salt | 270 | 87 |
| 7. DPSA + 4EO Na Salt | 280 | 81 |

Legend:
NPSA - nonylphenol sulfonic acid
DPSA - dodecylphenol sulfonic acid
EO - ethylene oxide The results shown in Table V indicated that these compounds had inadequate foam stability and half-life expectancy.

EXAMPLE 8

This example illustrates the emulsion stability of the compounds 1-7 utilizing 50 ml of solvent, 50 ml tap-water and 2 grams of each of the compounds. The compounds in Table VI were prepared in accordance with the procedure of Example 1, except dodecylphenol sulfonic acid was substituted where indicated below.

TABLE VI

| Sample | Solvent | Emulsion, Type & Stability |
|---|---|---|
| 1. NPSA + 4EO Na Salt | Xylene | Formed emulsion |
| 2. NPSA + 6EO Na Salt | Xylene | containing 30-60% foam |
| 3. NPSA + 2EO Na Salt | Xylene | Stable for 3 days at |
| 4. NPSA + 8EO Na Salt | Xylene | room temperature |
| 5. DPSA + 4EO Na Salt | Xylene | Stable for 3 days at room temperature |
| 6. DPSA + 2EO Na Salt | Xylene | Stable for 3 days at room temperature |
| 7. DPSA + 6EO Na Salt | Xylene | Stable for 3 days at room temperature |
| 8. NPSA + 4EO Na Salt | Kerosene | Formed emulsion |
| 9. NPSA + 6EO Na Salt | Kerosene | containing 30-60% foam |
| 10. NPSA + 2EO Na Salt | Kerosene | Stable for 3 days at |
| 11. NPSA + 8EO Na Salt | Kerosene | room temperature |
| 12. DPSA + 4EO Na Salt | Kerosene | Stable for 3 days at room temperature |
| 13. DPSA + 2EO Na Salt | Kerosene | Stable for 3 days at room temperature |
| 14. DPSA + 6EO Na Salt | Kerosene | Stable for 3 days at room temperature |
| 15. NPSA + 4EO Na Salt | Diesel | Formed emulsion |
| 16. NPSA + 6EO Na Salt | Diesel | containing 30-60% foam |
| 17. NPSA + 2EO Na Salt | Diesel | Stable for 3 days at |
| 18. NPSA + 6EO Na Salt | Diesel | room temperature |
| 19. DPSA + 4EO Na Salt | Diesel | Stable for 3 days at room temperature |
| 20. DPSA + 4EO Na Salt | Diesel | Stable for 3 days at room temperature |
| 21. DPSA + 4EO Na Salt | Diesel | Stable for 3 days at room temperature |

Legend:
NPSA - nonyphenol sulfonic acid
DPSA - dodecylphenol sulfonic acid
EO - ethylene oxide The data shown in Table VI indicates that the compounds 1 to 7 with the solvents (xylene, kerosene and diesel) form stable emulsions accompanied by considerable foam.

EXAMPLE 9

This paragraph illustrates the effectiveness of the sample compounds as hydrotropes. The compounds in Table VII were prepared in accordance with the procedure in Example 1, except dodecylphenol sulfonic acid was substituted where indicated below.

TABLE VII

| Sample | Cloud Point | Temperature |
|---|---|---|
| 1. NaDDBS with 5% NPSA + 2 EO Na | Cl. Pt. | 0° C. |
| 2. NaDDBS with 5% NPSA + 4 Eo Na | Cl. Pt. (−2) | 0° C. |

TABLE VII-continued

| Sample | Cloud Point | Temperature |
|---|---|---|
| 3. NaDDBS with 5% NPSA + 6 Eo Na | Cl. Pt. (−4) | 0° C. |
| 4. NaDDBS with 5% DPSA + 2 Eo Na | Cl. Pt. | 0° C. |
| 5. NaDDBS with 5% DPSA + 4 Eo Na | Cl. Pt. (−2) | −0,5° C. |
| 6. NaDDBS with 5% DPSA + 6 Eo Na | Cl. Pt. (−3) | 4° C. |
| 7. NaDDBS with 5% DPSA + 8 Eo Na | Cl. Pt. (−3) | −2° C. |
| 8. NaDDBS with no additive (control): | Cl. Pt. | 6° C. |
| 9. NaDDBS with 5% SXS (for comparison) | Cl. Pt. | 2° C. |

The Cloud point of a 20% NADDBS containing 5% (on dry basis) of additives was determined. The composition of solution:

| | |
|---|---|
| NaDDBSA (100%) | 20 gr. |
| Additive (100%) | 1 gr. |
| Water | 79 gr. |
| | 100 gr. |

The NaDDBS and additives were taken from conc. solutions with known conc.

The data shown in Table VII indicates that the compounds 1 to 7 when added to the NaDDBS solution were more effective as hydrotropes as compared to SXS which represents material used commercially.

EXAMPLE 10

This example illustrates the solubility of the sample compound at 10% in various solvents. The compounds in Table VIII were prepared in accordance with the procedure in Example 1, except dodecylphenol sulfonic acid was substituted where indicated below.

TABLE VIII

| Sample # | SOLVENT Water | IPA | A-150 | Kerosene |
|---|---|---|---|---|
| 1. NPSA + 4 EO Na Salt | Sol | Sol | Insol | Insol |
| 2. NPSA + 6 EO Na Salt | Sol | Sol | Insol | Insol |
| 3. NPSA + 2 EO Na Salt | Sol | Disp. | Insol | Insol |
| 4. DPSA + 8 EO Na Salt | Sol | Sol | Insol | Insol |
| 5. DPSA + 2 EO Na Salt | Sol | Sol | Insol | Insol |
| 6. DPSA + 6 EO Na Salt | Sol | Sol | Insol | Insol |
| 7. DPSA + 4 EO Na Salt | Sol | Sol | Insol | Insol |
| 8. DPSA + 4 EO $Ca^{++}$ Salt | Sol | Sol | Sol | Sol |

Legend:
NPSA - nonyphenol sulfonic acid
DPSA - dodecylphenol
EO - ethylene oxide The data shown in Table VIII illustrates the results of solubility tests run on compounds 1 to 7 in different solvents. The solubility of DPSA +4EO $Ca^{++}$ salt in water as well as kerosene is noteworthy.

EXAMPLE 11

A subterranean petroleum containing formation is located at a depth of 6000 feet. The formation is 40 feet thick and the perosity is 30%. The field is exploited first by means of a primary production utilizing a square grid pattern of 400 feet line spacing between wells. At the conclusion of primary recovery, which recovers only 25% of the original petroleum in place in the formation, injection wells are drilled in the center of the square grid to convert the field into an inverted 5-spot pattern for water injection. Although a large field entails a multiplicity of square grid patterns each being approximately the same length on the side, it is possible to analyze the field performance by considering only a single grid unit. Water is injected into the injection well and oil is recovered from the production well until the water-oil ratio reaches a value of about 40 at which point water flooding operations are concluded. Only 45% of the original oil in play has been recovered at the termination of water flooding operations, and some form of enhanced oil recovery operations must be resorted to in order to maintain significant amounts remaining petroleum.

The water present in the formation has a high salinity content and also contains high concentration of various cations. The temperature of the formation is approximately 400° F. Conventional surfactants cannot be utilized in this formation because of the high salinity, water hardness and high temperature. Thus, a surfactant composition should be utilized that exhibits excellent surface tension, lubricity, thermal stability and interfacial tension properties, such as the sodium salt of ethoxylated nonylphenol sulfonic acid wherein there are 3 ethylene oxide groups are attached to each available hydroxyl as shown in formula (1). The surfactant is mixed with at least 90% of aqueous medium and not more than 10% of the surfactant compound. The percentage of surfactant depends on various factors present in the formation.

Thus, while the invention has been described with reference to certain preferred embodiments, those skilled in the art will realize the changes and modifications may be made thereto without departing from the full and intended scope of appended claims.

EXAMPLE 12

A granular detergent base powder having the composition listed hereinafter was prepared by conventional spray-drying of the individual ingredients. The ingredients of composition I include linear, dodecylbenzene sulfonate sodium salt, tallow alcohol, sulfate sodium salt, sodium tripolyphosphate, sodium silicate solids, carboxymethylcellulose, copolymer of maleic anhydride and methyl vinyl ether sodium sulfate and moisture. Composition I is comparable to a analogous composition II except that 5% of the sodium salt ethoxylated of nonylphenol sulfonic acid is added. The results indicate that composition II is at least 2 times as effective as composition I in terms of solubility and rate of dissolution of the composition in water. Further, composition II has the added benefit of increasing the cleaning property of the detergent composition described above.

EXAMPLE 13

The sodium salt of ethoxylated nonylphenol sulfonic acid (NPSA+EO) is prepared in accordance with the procedure of Example 1. 5% of NPSA+EO is added to existing known fiber lubricants such as Tween-60, Diakeol 5, coconut oil and pluronic polyol L-31. The lubricity of these known fiber lubricants are compared to the lubricity of these known fiber lubricants with added 5% NPSA+EO. Fiber lubricants with 5% NPSA+EO added exhibit better lubricity characteristics when compared to the fiber lubricants without added NPSA+EO.

EXAMPLE 14

A series of 11 pre-weighed mild steel corrosion coupons are put into a solution of 2% aqueous sulfonic acid in a sealed glass container. The container is heated in an oven to 150° F. Four compositions are prepared with four corrosion inhibiting amines, namely 4-propyl-4-decylammonium sulfate, 7-pentyl-7-pentadecylammonium sulfate, ethoduomen T-13 [$RN(CH_2CH_2OH)(CH_3)_2$ $N(CH_2CH_2OH)_2$] where R is tallow and cocodimethylamine oxide [$C_{12}H_{25}N(CH_3)_2O$]. Four other compounds are prepared with same corrosion inhibiting amines with the sodium salt of ethoxylated nonylphenol sulfonic acid added as a surfactant. In each instant where corrosion inhibiting amine and surfactant (NPSA+EO) are utilized, the surfactant is present in 5% by weight of the total compound. These corrosion inhibiting compositions are added to the acid solutions at an overall concentration 100 ppm. After one or two days, each corrosion coupons weight loss is determined. The results indicate that the corrosion inhibiting solution containing NPSA+EO exhibits higher corrosion inhibiting properties as well as better antifouling characteristics than those compounds without added NPSA+EO.

EXAMPLE 15

7.51 grams of nonlyphenol+4EO sodium sulfonate (49.9% solids) is dissolved with stirring in 150 grams demineralized water. To this solution are added 105 grams of vinylacetate and 145 grams of n-butyl acrylate with stirring to form an emulsion. The pH of emulsion was adjusted to 4.0 by dropwise addition of dilute HCl. To a 2-liter 4-necked resin flask, jilted with stirrer, reflex condensor and thermometer, is added 50 grams of demineralized water which is stirred, purged with nitrogen and heated to 75° C. 3 ml of an initiator solution, consisting of 1 gram of sodium persulfate in 50 grams of demineralized water, is added to the resin flask. After 5 minutes the monomer emulsion is slowly added at a rate of 200 ml per hour along with the initiator solution at 20 ml per hour. The resulting polymer latex has a solids content of 45.4% and viscosity of 60 cps. The latex has an average particle sit of 0.29 microns.

EXAMPLE 16

A sized hemipentaacetate crepe fabric (raw material e.g. with a mixture of polyacrylates) is padded on a pad-roll installation with a liquor containing.

35 g/l of the commercially available dyestuff C.I. Disperse Orange 30

10 g/l of the commercially available dyestuff C.I. Disperse Red 167

20 g/l of the commercially available dyestfuff C.I. Disperse Blue 73

10 g/l (solids) of the commercially available size based on polyacrylate (Size T8, BASF), dissolved in water 5 g/l (solids) of a commercially available size based on polyvinyl alcohol (Varinol, Hoechst)

35 g/l of the sodium salt of nonylphenol sulfonic acid 15 g/l hexylene glycol, and 2 g/l ammonium sulphate.

The liquor is adjusted to a pH of 5 with acetic acid. The fabric is squeezed to 40% pickup based on the dry weight of the fabric and maintained at 80° for 3 hours. The fabric is an even dark brown color.

There is obtained an even dark brown dyeing.

EXAMPLE 17

The sodium salt of ethoxylated nonylphenol sulfonic acid (NPSA+EO) is prepared in accordance with the procedure of Example 1. 5% of NPSA+EO is added to existing known fiber lubricants such as Tween-60, Diakeol 5, coconut oil and pluronic polyol L-31. The lubricity of these known fiber lubricants are compared to the lubricity of these known fiber lubricants with added 5% NPSA+EO. Fiber lubricants with 5% NPSA+EO added exhibit better lubricity characteristics when compared to the fiber lubricants without added NPSA+EO.

What is claimed is:

1. A method of improving the effectiveness of corrosion inhibitors selected from the group consisting of primary, secondary and tertiary aliphatic or aromatic amines and derivatives thereof, which comprises adding to said inhibitor about 1% to about 10% weight of a compound having the general formula

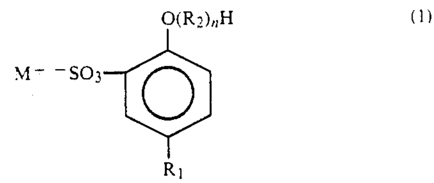

wherein $R_1$ is nonyl or dodecyl, $R_2$ is ethylene oxide, $M^+$ is selected from the group consisting of $N_a$, K, Li, Ca, Ba, Sr, Mg, Zn and amine salts thereof, and n is an integer from 1 to about 4.

2. A method according to claim 1, wherein said compounds of formula (1) are added in the range of about 2% to about 5% weight.

3. A method according to claim 1, wherein $R_1$ is an alkyl group having 9 carbon atoms, $M^+$ is Na and n is 3.

4. A method according to claim 1, wherein $R_1$ is an alkyl group having 9 carbon atoms, $M^+$ is $Ca^{++}$ and n is 3.

5. A method according to claim 1, wherein $R_1$ is an alkyl group having 12 carbon atoms, $M^+$ is Na and n is 4.

6. A method according to claim 1, wherein $R_1$ is an alkyl group having 12 carbon atoms, $M^+$ is $Ca^{++}$ and n is 4.

* * * * *